United States Patent
Hartley et al.

(10) Patent No.: US 9,504,589 B2
(45) Date of Patent: Nov. 29, 2016

(54) STENT DELIVERY SYSTEM WITH NITINOL TRIGGER WIRE

(75) Inventors: David Ernest Hartley, Wannanup (AU); Darin G. Schaeffer, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 461 days.

(21) Appl. No.: 13/504,588

(22) PCT Filed: Oct. 27, 2010

(86) PCT No.: PCT/US2010/054252
§ 371 (c)(1),
(2), (4) Date: Jun. 5, 2012

(87) PCT Pub. No.: WO2011/059707
PCT Pub. Date: May 19, 2011

(65) Prior Publication Data
US 2012/0239130 A1 Sep. 20, 2012

Related U.S. Application Data

(60) Provisional application No. 61/280,036, filed on Oct. 29, 2009.

(51) Int. Cl.
*A61F 2/82* (2013.01)
*A61F 2/95* (2013.01)

(52) U.S. Cl.
CPC .......... *A61F 2/95* (2013.01); *A61F 2002/9505* (2013.01); *A61F 2002/9511* (2013.01)

(58) Field of Classification Search
CPC ............. A61F 2/95; A61F 2002/9505; A61F 2002/9511
See application file for complete search history.

(56) References Cited

U.S. PATENT DOCUMENTS

| | | |
|---|---|---|
| 2003/0225446 A1 | 12/2003 | Hartley |
| 2003/0233140 A1* | 12/2003 | Hartley et al. ............... 623/1.11 |
| 2004/0193244 A1* | 9/2004 | Hartley et al. ............... 623/1.12 |
| 2005/0085890 A1* | 4/2005 | Rasmussen et al. ......... 623/1.11 |

(Continued)

FOREIGN PATENT DOCUMENTS

| | | |
|---|---|---|
| JP | 2009-521281 | 6/2009 |
| WO | WO96/18361 | 6/1996 |

(Continued)

OTHER PUBLICATIONS

International Search Report and Written Opinion for PCT/US2010/054252 dated Feb. 25, 2011, 11 pgs.

(Continued)

*Primary Examiner* — Todd J Scherbel
(74) *Attorney, Agent, or Firm* — Brinks Gilson & Lione

(57) ABSTRACT

A stent graft delivery system (50) has a stent graft (74) retained on it. The stent graft has an exposed proximally extending self expanding stent (76) which is retained in a distally opening capsule (78) at the distal end of a nose cone dilator (58) on the delivery system. A trigger wire (80) extends from a release mechanism (82) the distal end of the delivery system into a first aperture (84) in the capsule, around a proximal bend (86) of the exposed stent and out of the first aperture in the capsule and extending proximally into a second aperture (88). The trigger wire prevents premature release of the exposed stent.

13 Claims, 6 Drawing Sheets

(56) References Cited

U.S. PATENT DOCUMENTS

2005/0222669 A1* 10/2005 Purdy .................. 623/1.13
2010/0331948 A1* 12/2010 Turovskiy et al. .......... 623/1.11
2011/0144735 A1* 6/2011 Hartley et al. ............... 623/1.11

FOREIGN PATENT DOCUMENTS

| WO | WO2005/034811 | 4/2005 |
| WO | WO2005/037142 | 4/2005 |
| WO | WO2007/076114 | 7/2007 |

OTHER PUBLICATIONS

Office Action for Japanese Patent Application No. 2012-536992 dated May 13, 2014, 7 pgs. Including English translation.
International Preliminary Report on Patentability for PCT/US2010/054252 dated May 1, 2012, 6 pages.
Office Action for Japanese Patent Application No. 2012-536992 dated Mar. 3, 2015, 4 pgs. including English translation.

* cited by examiner

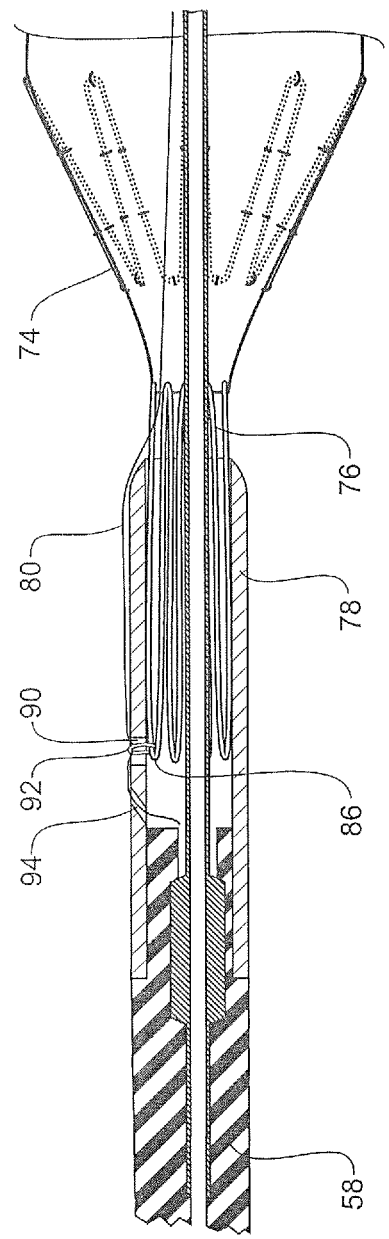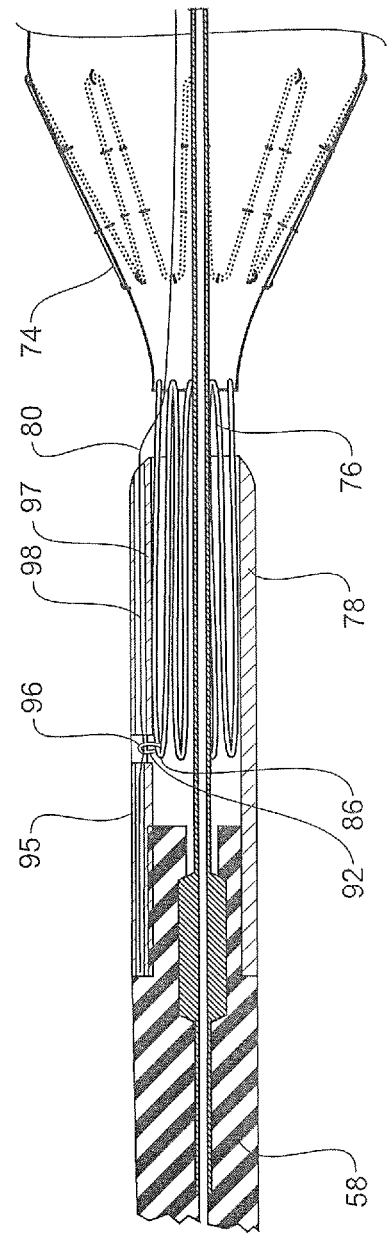
Fig 4
Fig 5

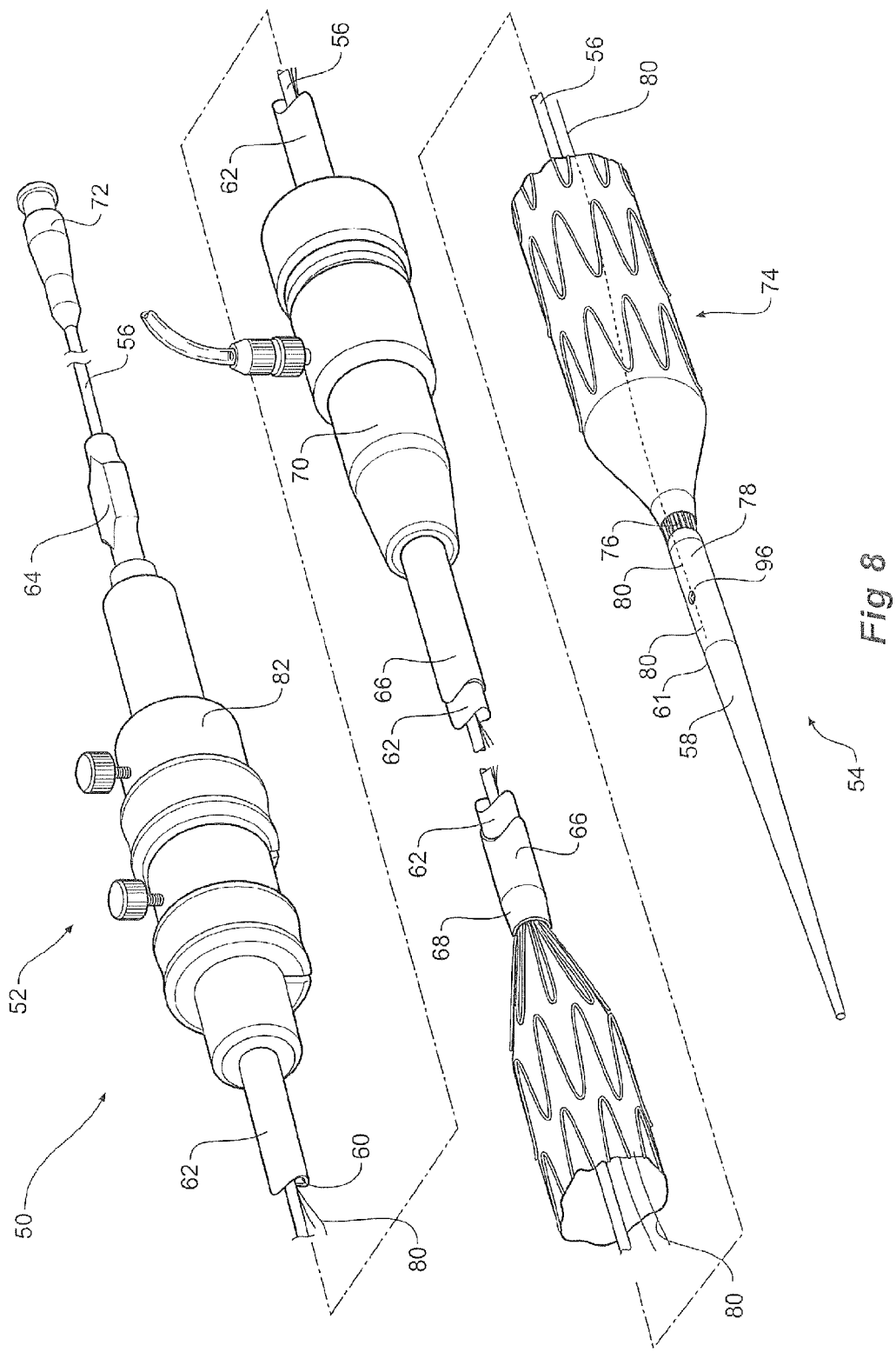

STENT DELIVERY SYSTEM WITH NITINOL TRIGGER WIRE

RELATED APPLICATIONS

The present patent document is a §371 filing based on PCT Application Serial. No. PCT/US2010/054252, filed Oct. 27, 2010 (and published as WO 2011/059707A1 on May 19, 2011), designating the United States and published in English, which claims the benefit of the filing date under 35 U.S.C. §119(e) of Provisional U.S. Patent Application Ser. No. 61/280,036, filed Oct. 29, 2009. All of the foregoing applications are hereby incorporated by reference in their entirety.

TECHNICAL FIELD

This disclosure relates to a medical device and more particularly to a medical device for introduction of an implantable device into the human or animal body.

BACKGROUND ART

An implantable device such as a stent graft can include a exposed self expanding stent which in use can expand and engage against the wall of a vessel such as the aorta and assist in retaining the implantable device in its desired position. Such an exposed self expanding stent can include barbs to assist with engagement and retention in the desired position. During introduction it is necessary to keep the exposed stent in a contracted condition and for this purpose a stent graft delivery device can include a capsule into which the exposed stent is received. The capsule also prevents the barbs from premature engagement with a vessel wall.

U.S. Pat. No. 7,435,253 issued on Oct. 14, 2008 and entitled "Prosthesis and a Method of Deploying a Prosthesis" discloses a stent graft introducer incorporating a capsule retention system and the teachings therein are incorporated herein in their entirety.

Premature release of the exposed stent from the capsule could cause problems to a patient and hence there has been proposed a trigger wire release system using a thin stainless steel wire which extends from a distal end of an introduction device and engages a proximal bend of the exposed stent inside the capsule.

It is desirable to use thinner and more flexible trigger wires but the prior art arrangements for trigger wire release system are not suitable with more flexible wires.

It is the object of this disclosure to provide a improved exposed stent retention system or at least provide a physician with a useful alternative device.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

DISCLOSURE OF THE INVENTION

In one form the disclosure comprises a stent graft delivery system in combination with a stent graft retained on the delivery system; the stent graft comprising an exposed self expanding stent and the exposed stent comprising at least one bend;

the delivery system comprising a distal end to remain outside of a patient in use and a proximal end to be introduced into the patient in use, the delivery system comprising a capsule to receive the exposed self expanding stent and to hold the exposed stent in a contracted condition during delivery thereof and a retention system to prevent premature removal of the exposed stent from the capsule;

the retention system comprising a first aperture and a second aperture in the capsule, the retention system further comprising a trigger wire extending from the distal end of the delivery system into the first aperture in the capsule, the wire engaging the bend of the exposed stent and then extending into the second aperture, wherein the exposed stent cannot be removed from the capsule until the trigger wire has been withdrawn.

The trigger wire can comprises an nickel titanium alloy wire such as nitinol wire and comprises a diameter of 0.016 to 0.018 inches.

The trigger wire can directly engage the bend of the exposed stent or can engage a retention loop and the retention loop engage the bend of the exposed stent. The retention loop can comprise a biocompatible material, a suture or a nitinol ring.

In one embodiment the capsule can comprise a cylindrical wall, at least a portion of which has a selected thickness, the first aperture comprises an aperture in the cylindrical wall extending through the thickness of the wall and the second aperture comprises an aperture extending longitudinally through the wall, the first and second apertures intersecting.

In an alternate form the disclosure comprises a stent graft delivery system in combination with a stent graft retained on the delivery system;

the stent graft comprising a proximally extending exposed self expanding stent and the exposed stent comprising at least one bend;

the delivery system comprising a distal end to remain outside of a patient in use and a proximal end to be introduced into the patient in use, the delivery system comprising a distally opening capsule at a distal end of a nose cone dilator, the capsule receiving the exposed proximally extending self expanding stent to hold the exposed stent in a contracted condition during delivery thereof, and a retention system for the exposed stent in the capsule;

the retention system comprising an first aperture in the capsule and a second aperture proximally of the first aperture, the retention system further comprising a trigger wire extending from the distal end of the delivery system into the first aperture in the capsule, engaging the proximal bend of the exposed stent and out of the first aperture in the capsule and then extending proximally into the second aperture.

In one embodiment the engagement of the proximal bend with the trigger wire comprises the proximal bend being bent toward the first aperture to engage the trigger wire.

In an alternate form the disclosure comprises a stent graft delivery system in combination with a stent graft retained on the delivery system;

the stent graft comprising a proximally extending exposed self expanding stent and the exposed stent comprising at least one bend;

the delivery system comprising a distal end to remain outside of a patient in use and a proximal end to be introduced into the patient in use, the delivery system comprising a distally opening capsule at a distal end of a nose cone dilator, the capsule comprising a cylindrical wall, at least a portion of which has a selected thickness, a first aperture in the cylindrical wall extending through the thickness of the wall and a second aperture extending longitudinally through the wall, the first and second apertures intersecting, the capsule receiving the exposed proximally extending self expanding stent to hold the exposed stent in a contracted condition during delivery thereof, and a retention system for the exposed stent in the capsule, the retention system further comprising a trigger wire extending from the distal end of the delivery system into the second aperture in the capsule, engaging the proximal bend of the exposed stent at the first aperture.

In an alternate form the disclosure comprises an endovascular delivery device in combination with an endoluminal prosthesis, the delivery device comprising;

a catheter body;

a guide wire catheter extending from the catheter body to a nose cone dilator at a proximal end of the delivery device;

a trigger wire release mechanism disposed at the distal end of the delivery device;

at least one trigger wire;

the endoluminal prosthesis comprising a distal end and a proximal end, a lumen and at least one stent and being disposed on the delivery device;

a proximal retention device disposed along at least part of the length of an outside surface of the guide wire catheter between the catheter body and the nose cone dilator, the proximal retention device comprising:

a main inner lumen, a secondary outer lumen concentric to the main inner lumen, and at least one aperture adjacent the proximal end;

the at least one stent being received in the main inner lumen of the proximal is retention device; and at least one retention loop engaging the at least one stent within the man inner lumen and the trigger wire at the aperture of the retention device;

where the trigger wire extends from the trigger release mechanism, through the proximal end of the endoluminal prosthesis, into the secondary outer lumen, out the aperture of the secondary outer lumen and through the retention loop and then continuing in the secondary outer lumen;

where the trigger wire restrains the endovascular prosthesis prior to withdrawal of the trigger wire; and where the trigger wire retains a substantially straight configuration during retention within the secondary outer lumen and during withdrawal of the trigger wire.

It will be seen that by these various arrangement the trigger wire enters the capsule through the first aperture, passes around the bend of the exposed stent and exits the capsule though the same elongate aperture and then enters another aperture in the nose cone dilator. By this arrangement the inventor has found that the trigger wire does not allow the exposed stent to be pulled out prematurely.

BRIEF DESCRIPTION OF THE DRAWINGS

This then generally describes the disclosure but to assist with understanding reference will be made to the accompanying drawings which show the prior art arrangement and an embodiment of the present disclosure.

In the drawings:

FIG. 4 shows a cross sectional view of an alternative embodiment of retention system according to the present disclosure;

FIG. 5 shows a cross sectional view of a further alternative embodiment of retention system according to the present disclosure;

FIG. 8 shows a implantable device delivery device according to one embodiment of the present disclosure incorporating the retention system shown in FIG. 5.

BEST MODE FOR CARRYING OUT THE INVENTION

Figure 1A:
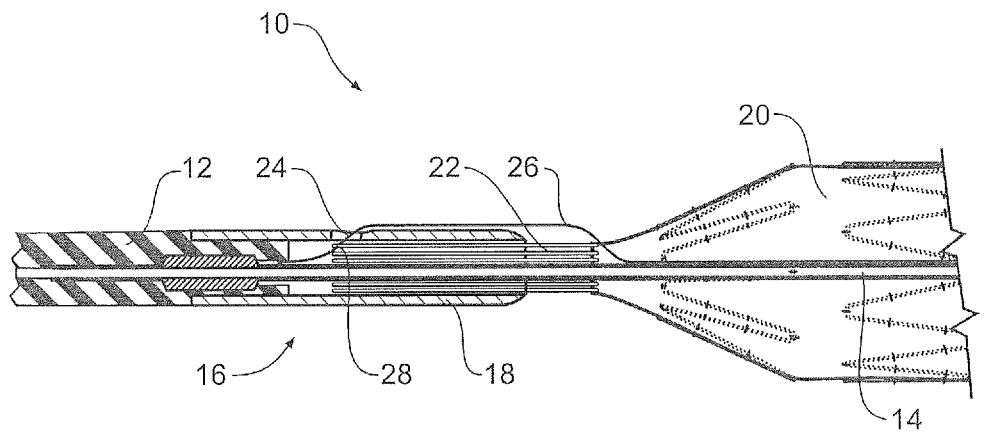
FIGS. 1A and 1B show a prior art trigger wire arrangement.
Figure 1B:
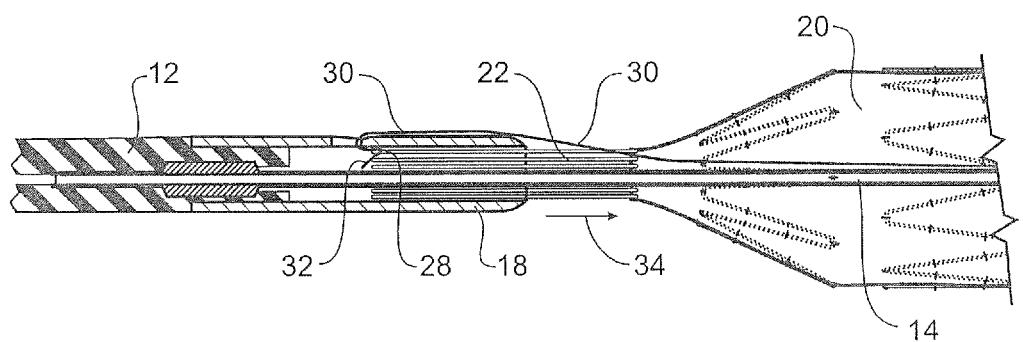

FIGS. 1A and 1B show a prior art trigger wire arrangement. In the prior art a delivery device 10 has a proximal end which includes (as shown in longitudinal cross section) a nose cone dilator 12 on a guide wire cannula 14. At the distal end 16 of the nose cone dilator 12 is a distally opening capsule 18. A stent graft 20 has a proximal exposed stent 22 which is contracted and is received into the capsule 18. The capsule has a small aperture 24 in the side of the capsule nearer its proximal end. A stainless steel trigger wire 26 passes through the aperture 24 and engages a bend 28 of the exposed stent 22. The wire then extends proximally within the capsule.

The stainless steel trigger wire 26 is inherently sufficiently rigid so that if the exposed stent is pulled distally under normal forces the wire will not release from its engagement with the bend 28 of the exposed stent.

If, however, the stainless steel wire of FIG. 1A is replaced with a nickel titanium alloy wire, such as nitinol wire, which is more flexible then the situation as shown in FIG. 1B can occur. Under normal forces on the exposed stent the nitinol wire 30 can bend much more easily so that the exposed stent 22 can pull back distally as shown by the arrow 34 and eventually the end 32 of the wire 30 can become disengaged from the bend 28 and the exposed stent can come out of the capsule prematurely. Movement sufficient to prematurely remove the exposed stent from the capsule may occur, for instance, when a sheath is being withdrawn from a stent graft or when a stent graft, while still retained on a delivery device, is being manipulated to correctly position it.

Figure 2:
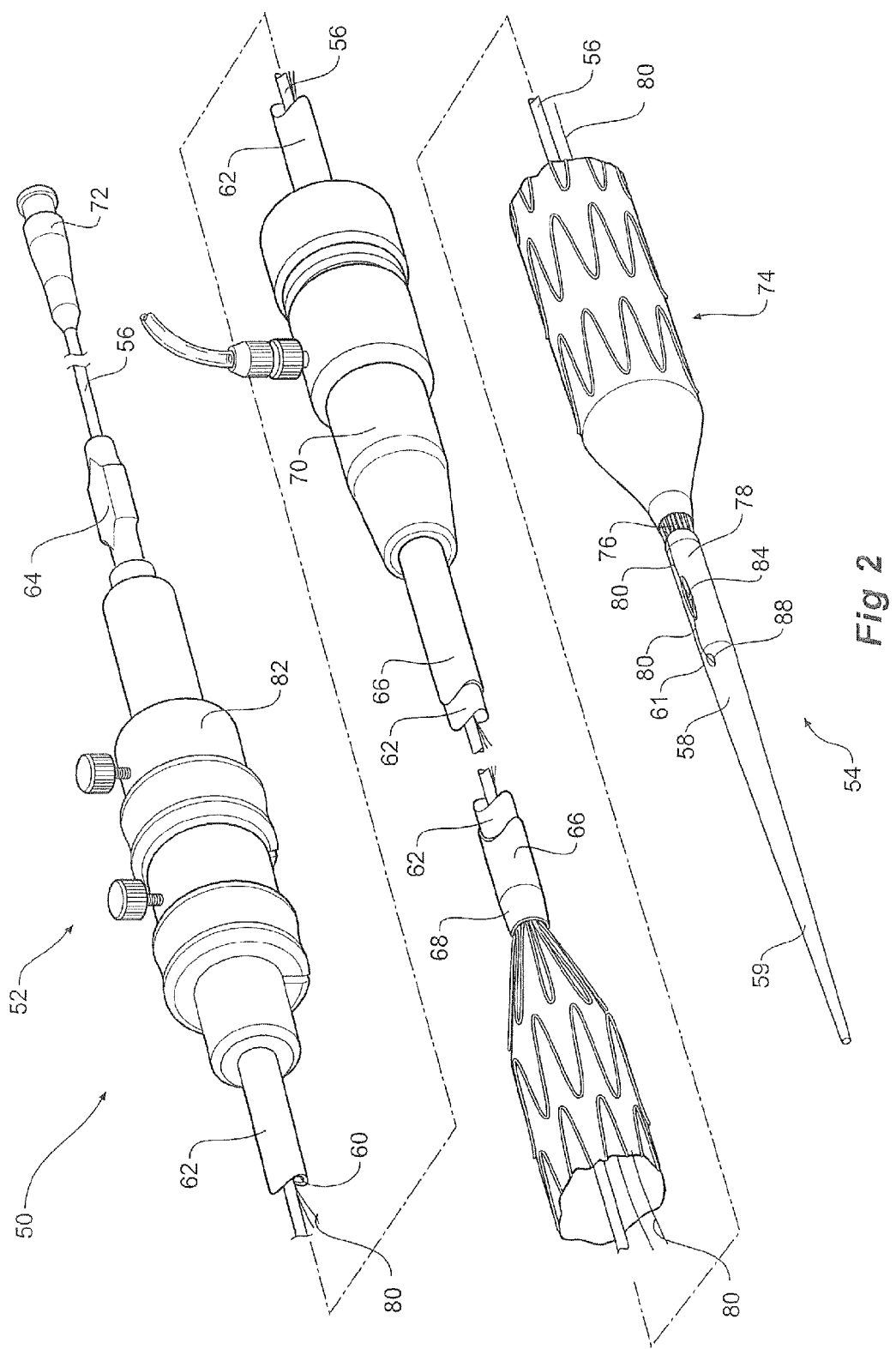
FIG. 2 shows a implantable device delivery device according to one embodiment of the present disclosure.
Figure 3A:
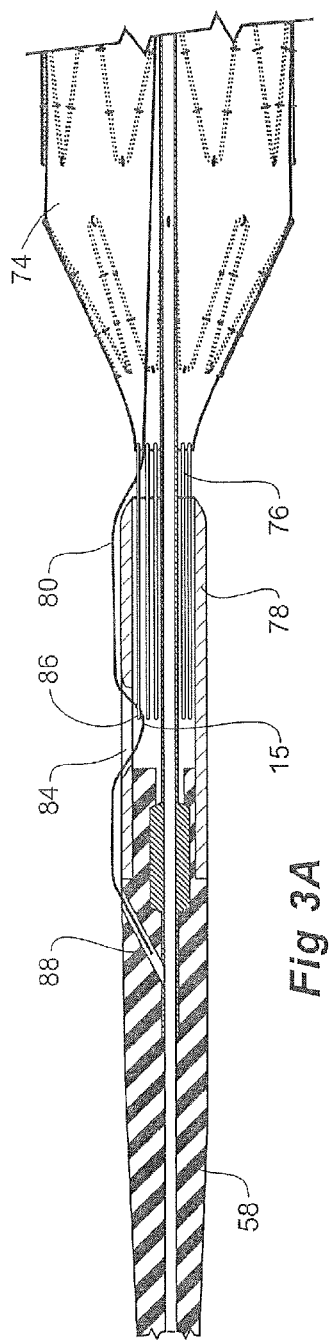
FIGS. 3A, 3B and 3C show detail of the capsule region of the embodiment shown in FIG. 2.
Figure 3B:
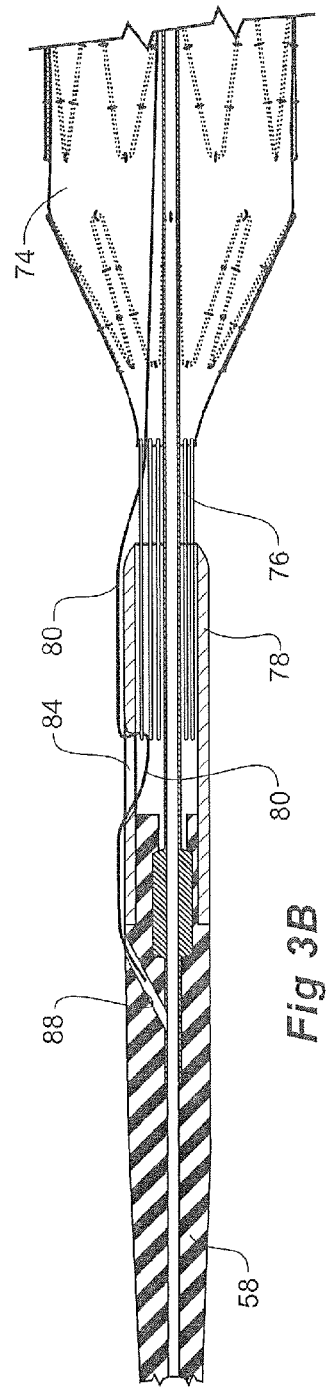
Figure 3C:
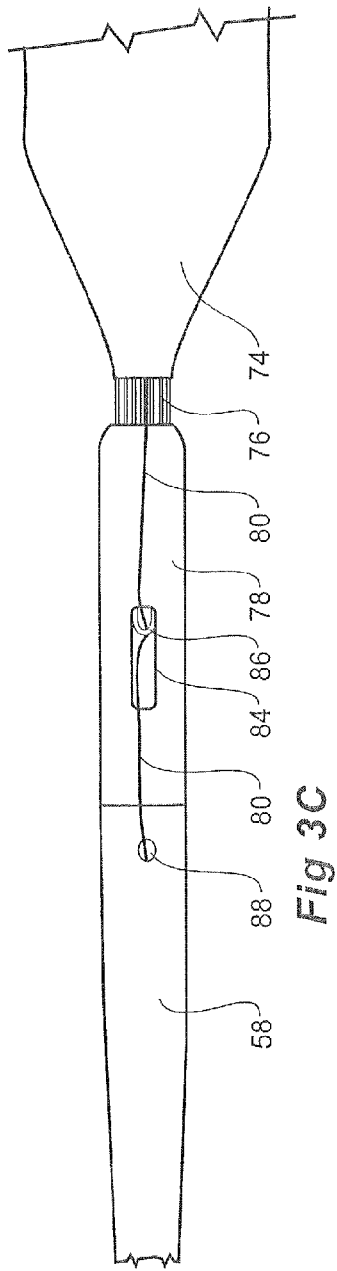

FIG. 2 shows a implantable device delivery device according to one embodiment of the present disclosure. FIGS. 3A and 3B show detail in longitudinal cross section and FIG. 3C shows a side view of the capsule region of the embodiment shown in FIG. 2.

The delivery device 50 has a handle portion 52 which in use remains outside a patient and an introduction portion 54 which is introduced into a patient to deliver a stent graft therein. The delivery device is depicted in FIG. 2 at a stage where a sheath has been partially withdrawn to expose the stent graft but stent graft has not yet been released from the delivery device. This particular configuration would normally only occur when the introduction portion 54 of the delivery device 50 is within a patient.

The handle portion 52 of the delivery device 50 has a guide wire cannula 56 which extends from distal of the handle portion 52 to and through a proximal tapered nose cone dilator 58 at the proximal end of the introduction portion 54. The guide wire cannula 56 extends longitudinally through a passageway or lumen 60 of a pusher or delivery catheter 62 which is connected to the handle portion 52 at its distal end. The guide wire cannula 56 can move longitudinally and rotationally with respect to the pusher catheter 62 and can be fixed with respect to the handle portion 52 and the pusher catheter 62 by a pin vice 64 at the distal end of the handle portion 52. An introducer sheath 66 fits coaxially around the delivery catheter 62 and extends from a tapered proximal end 68 which optionally includes a radiopaque marker (not shown) to a connector valve and manipulator 70 mounted onto the sheath 62. A well-known male Luer lock connector hub 72 is attached at the distal end of the guide wire cannula 56 for connection to syringes and other medical apparatus.

The connector valve and manipulator 70 may be an automatically sealing valve comprising a haemostatic seal assembly including a silicone disc assembly and the pusher catheter and the auxiliary catheter extending through the silicone disc assembly. Alternatively the valve assembly can include a manually operable valve such as the Captor Valve (Cook Inc, Bloomington, Ind.)

The introducer sheath 66 extends proximally to the nose cone dilator 58 and covers the stent graft 74 during introduction of the deployment device into a patient. As shown in FIG. 2 the introducer sheath 66 has been withdrawn distally to expose the stent graft 74 which is a stage which occurs during deployment when the deployment device is in a selected position within the vasculature of a patient.

The stent graft or implantable device 74 is carried on the guide wire cannula 56 proximally of the delivery catheter 62 and distally of the nose cone dilator 58. Nose cone dilator 58 includes a tapered proximal end 59 for accessing and dilating a vascular access site over a well-known and commercially available wire guide (not shown) extending through the guide wire cannula 56.

The stent graft 74 has a proximally extending exposed stent 76 which is received into a distally opening capsule 78 which is on the distal end 61 of the nose cone dilator 58.

A trigger wire release system, to enable release of the stent graft from the proximal end 54 of the delivery device 50 when the stent graft is correctly positioned provides a proximal retention system. A trigger wire 80 extends from a proximal trigger wire release 82 on the handle 52 through the lumen 60 of the delivery catheter 62 and through the stent graft 74 and exiting from the stent graft in the region of the exposed proximal stent 76. From there the wire extends along the outside of the capsule and enters a first aperture 84 in the wall of the capsule 78 and under a bend 86 of the exposed stent 76. The wire 80 then exits the aperture 84 and extends proximally and enters a second aperture 88 in the nose cone dilator 58 and terminates within the aperture 88. See FIGS. 3A and 3C for detail of the placement of the trigger wire 80.

If the exposed stent is pulled distally as may happen during manipulation of the stent graft to correctly position it longitudinally and rotationally the position as shown in FIG. 3B can occur. In this situation the bend 86 of the exposed stent 76 can pull back to the distal end of the aperture 84 but the placement of the wire 80 is such that it will not allow the stent to be pulled any further.

In a test of an assembly of the type depicted in FIG. 2 it was found that a distal pull on the stent graft of about 40 Newtons did not cause distortion of the trigger wire or withdrawal of the exposed stent from the capsule. In a further test a loading was applied to the stent graft in a distal direction such as would occur when a sheath was being withdrawn from a stent graft within the vasculature of a patient. With such a pre-loading on the stent graft the pull out force for the trigger wire was tested. At a pre-load of 10 n the pull out force was 4.8 n. At a pre-load of 20 n the pull out force was 10 n. These pull out forces were within acceptable levels for trigger wire retraction.

FIG. 4 shows a cross sectional view of an alternative embodiment of retention system according to the present disclosure. In this embodiment the same reference numerals are used for corresponding items to those in FIGS. 2 and 3A.

Figure 7A:
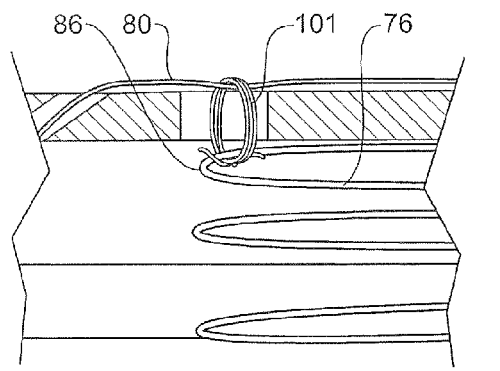
FIGS. 7A, 7B, 7C and 7D show alternative arrangement of retention loops.
Figure 7B:
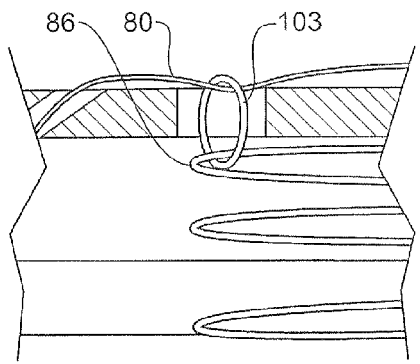
Figure 7C:
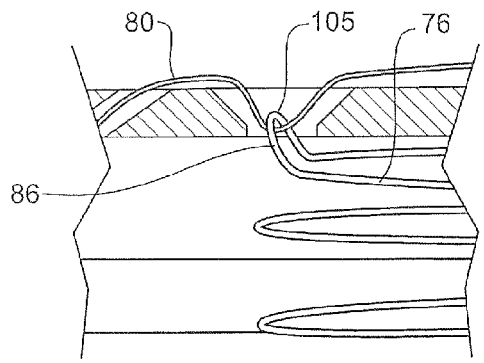

In this embodiment the stent graft 74 has a proximally extending exposed stent 76 which is compressed and received into a distally opening capsule 78 which is on the distal end 61 of the nose cone dilator 58. A trigger wire release system, to enable release of the stent graft from the proximal end 54 of the delivery device 50 when the stent graft is correctly positioned provides at a least proximal retention system. A trigger wire 80 extends from a proximal trigger wire release on the handle (not shown) and exits from the stent graft in the region of the exposed proximal stent 76. From there the wire extends along the outside of the capsule and passes over a first aperture 90 in the wall of the capsule 78 without entering a lumen of the capsule 78, and there engages a retention loop 92 which in turn is engaged with a bend 86 of the exposed stent 76. The wire 80 then extends proximally and enters a second aperture 94 which is proximal of the aperture 90 and the wire terminates within the second aperture 94. Various embodiments of retention loop are shown in FIGS. 7A to 7C.

Figure 6:
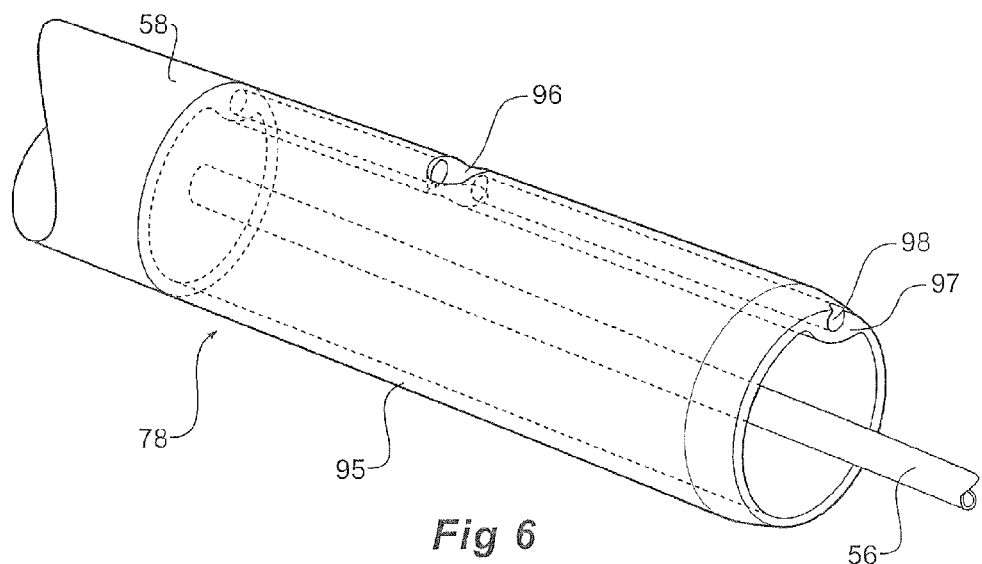
FIG. 6 shows detail of the capsule portion of the embodiment shown in FIG. 5.

FIG. 5 shows a cross sectional view of a further alternative embodiment of retention system according to the present disclosure, FIG. 6 shows detail of the capsule portion of the embodiment shown in FIG. 5 and FIG. 8 shows a implantable device delivery device according to one embodiment of the present disclosure incorporating the retention system shown in FIGS. 5 and 6. In this embodiment the same reference numerals are used for corresponding items to those in FIGS. 2 and 3A.

In this embodiment the stent graft 74 has a proximally extending exposed stent 76 which is received into a distally opening capsule 78 which is on the distal end 61 of the nose cone dilator 58. The capsule has a peripheral wall 95. The peripheral wall 95 has a longitudinal thickened region 97 and a first aperture 96 extending through the thickened region 97 of the wall 95. A second aperture 98 extends through the length of the thickened region 97 of the wall 95 and intersects with the first aperture 96 within the wall. The second aperture 98 extends within the wall of the capsule substantially o the full length of the capsule 78. A trigger wire release system, to enable release of the stent graft from the proximal end of the delivery device when the stent graft is correctly positioned provides a proximal retention system. A trigger wire 80 extends from a proximal trigger wire release on the handle (not shown) and exits from the stent graft 74 in the region of the exposed proximal stent 76. From there the wire extends is towards the capsule and enters the second aperture 98. At the intersection with the first aperture 96 the wire 80 passes through a retention loop 92 which in turn is engaged with a bend 86 of the exposed stent 76. The wire 80 then extends proximally. Various embodiments of retention loop are shown in FIGS. 7A to 7C.

FIGS. 7A, 7B, 7C and 7D show alternative arrangement of retention loops.

In FIG. 7A the retention loop 101 which engages between the trigger wire 80 and the bend 86 of the exposed stent 76 is formed from a biocompatible thread such as a suture material.

In FIG. 7B the retention loop 103 which engages between the trigger wire 80 and the bend 86 of the exposed stent 76 is formed from a circular or elliptical ring of metal such as stainless steel or a nickel titanium alloy such as nitinol wire.

In FIG. 7C the retention loop which engages the trigger wire 80 comprises the bend 86 of the exposed stent 76 being formed into an eyelet 105 through which the trigger wire passes.

Figure 7D:
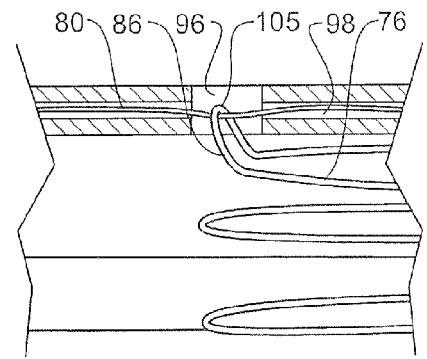

In FIG. 7D the retention loop 105 is used with the embodiment shown in FIG. 5. In this case the retention loop comprises the bend 86 of the exposed stent 76 being bent towards the first aperture and formed into an eyelet 105 which extends into the first aperture 96 for a sufficient distance that the trigger wire 80 extending through the second aperture 98 passes through the eyelet 105. In this embodiment the trigger wire 80 retains a substantially straight configuration during retention within the secondary outer lumen and during withdrawal of the trigger wire. This will reduce the retraction force of the trigger wire while preventing premature release of the exposed stent.

Throughout this specification various indications have been given as to the scope of this disclosure but the disclosure is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The invention claimed is:

1. A stent graft delivery system in combination with a stent graft retained on the delivery system;
   the stent graft comprising an exposed self expanding stent and the exposed stent comprising at least one bend;
   the delivery system comprising a distal end to remain outside of a patient in use and a proximal end to be introduced into the patient in use, the delivery system comprising a capsule to receive the exposed self expanding stent and to hold the exposed stent in a contracted condition during delivery thereof and a retention system to prevent premature removal of the exposed stent from the capsule;
   the retention system comprising a first aperture and a second aperture in the capsule, the retention system further comprising a trigger wire that extends from the distal end of the delivery system, then extends along a distal exterior surface of the capsule, then enters the first aperture in the capsule, then engages the bend of the exposed stent, then exits the first aperture, then extends along a proximal exterior surface of the capsule, and then enters the second aperture, wherein the exposed stent cannot be removed from the capsule until the trigger wire has been withdrawn.

2. The combination as in claim 1 wherein the trigger wire comprises a nickel titanium alloy wire.

3. The combination as in claim 1 wherein the trigger wire comprises a diameter of 0.016 to 0.018 inches.

4. The combination as in claim 1 wherein the trigger wire directly engages the bend of the exposed stent.

5. The combination as in claim 1 wherein the trigger wire engages a retention loop through the first aperture and the retention loop engages the bend of the exposed stent.

6. The combination as in claim 5 wherein the retention loop comprises a material selected from suture material or nitinol.

7. The combination as in claim 1 wherein the delivery device comprises a proximal dilator and the capsule is at a distal end of the dilator and the capsule comprises a distally facing open end and the exposed self expanding stent comprises a proximally extending exposed stent and the proximally extending exposed stent is received in the distally facing open end of the capsule and the second aperture is in the dilator.

8. A stent graft delivery system in combination with a stent graft retained on the delivery system;
   the stent graft comprising a proximally extending exposed self expanding stent and the exposed stent comprising at least one bend;
   the delivery system comprising a distal end to remain outside of a patient in use and a proximal end to be introduced into the patient in use, the delivery system comprising a distally opening capsule at a distal end of a nose cone dilator, the capsule receiving the exposed proximally extending self expanding stent in a lumen of the capsule to hold the exposed stent in a contracted condition during delivery thereof, and a retention system for the exposed stent in the capsule;
   the retention system comprising a first aperture in the capsule and a second aperture proximally of the first aperture, the retention system further comprising a trigger wire extending from the distal end of the delivery system, then passing over the first aperture in the capsule without entering the lumen of the capsule, being coupled to the at least one bend of the exposed stent while passing over the first aperture, and then extending proximally into the second aperture.

9. The combination as in claim 8 wherein the trigger wire comprises a nickel titanium alloy wire such as Nitinol wire and comprises a diameter of 0.016 to 0.018 inches.

10. The combination as in claim 9 wherein the engagement of the at least one bend with the trigger wire comprises a retention loop selected from a biocompatible material, a suture loop and a nitinol ring.

11. The combination as in claim 9 wherein the exposed stent comprises the at least one bend being bent toward the first aperture to engage the trigger wire.

12. A stent graft delivery system in combination with a stent graft retained on the delivery system;
   the stent graft comprising a proximally extending exposed self expanding stent and the exposed stent comprising at least one bend;
   the delivery system comprising a distal end to remain outside of a patient in use and a proximal end to be introduced into the patient in use, the delivery system comprising a distally opening capsule at a distal end of a nose cone dilator, the capsule comprising a cylindrical wall, at least a portion of which has a selected thickness, a first aperture in the cylindrical wall extending through the thickness of the wall and a lumen extending longitudinally through the wall, the first aperture and the lumen intersecting within the wall,
   the exposed proximally extending self expanding stent disposed within a second lumen of the capsule such that the exposed stent is held in a contracted condition during delivery thereof, and a retention system for the exposed stent in the capsule, the retention system further comprising a trigger wire that extends from the distal end of the delivery system into the lumen in the capsule, the trigger wire not entering the second lumen of the capsule, the trigger wire engaging the at least one bend of the exposed stent at the first aperture.

13. The combination as in claim 12 wherein the engagement of the at least one bend with the trigger wire comprises a retention loop selected from a biocompatible material, a suture loop and a nitinol ring.

* * * * *